(12) United States Patent
Roberts

(10) Patent No.: US 9,241,054 B1
(45) Date of Patent: Jan. 19, 2016

(54) PROTECTIVE CASE WITH INTEGRATED BREATHALYZER

(71) Applicant: Kyle Shane Roberts, Las Vegas, NV (US)

(72) Inventor: Kyle Shane Roberts, Las Vegas, NV (US)

( * ) Notice: Subject to any disclaimer, the term of this patent is extended or adjusted under 35 U.S.C. 154(b) by 0 days.

(21) Appl. No.: 14/728,481

(22) Filed: Jun. 2, 2015

Related U.S. Application Data

(60) Provisional application No. 62/025,184, filed on Jul. 16, 2014.

(51) Int. Cl.
| | |
|---|---|
| *G01N 1/22* | (2006.01) |
| *H04M 1/21* | (2006.01) |
| *G01N 33/497* | (2006.01) |
| *H04B 1/3888* | (2015.01) |
| *G01N 31/00* | (2006.01) |

(52) U.S. Cl.
CPC ............. *H04M 1/21* (2013.01); *G01N 33/4972* (2013.01); *H04B 1/3888* (2013.01)

(58) Field of Classification Search
CPC ................ G01N 33/497; G01N 33/98; G01N 2001/2244; G01N 2800/307; A61B 2010/0087; B60K 28/063; A61M 2016/0036
See application file for complete search history.

(56) References Cited

U.S. PATENT DOCUMENTS

| | | | | |
|---|---|---|---|---|
| 6,790,178 | B1* | 9/2004 | Mault et al. | 600/300 |
| 2004/0236244 | A1* | 11/2004 | Allen et al. | 600/532 |
| 2007/0093725 | A1* | 4/2007 | Shaw | 600/543 |
| 2011/0079073 | A1* | 4/2011 | Keays | 73/23.3 |
| 2011/0102182 | A1* | 5/2011 | Ohya | 340/576 |
| 2011/0136555 | A1* | 6/2011 | Ramies et al. | 455/575.8 |
| 2011/0233078 | A1* | 9/2011 | Monaco et al. | 206/223 |
| 2011/0253569 | A1* | 10/2011 | Lord | 206/320 |
| 2012/0031166 | A1* | 2/2012 | Lopez et al. | 73/23.3 |

\* cited by examiner

*Primary Examiner* — Jill Warden
*Assistant Examiner* — Brittany Fisher

(57) ABSTRACT

An apparatus includes a protective case for a portable computing device and an integrated alcohol sensor module for measuring the blood alcohol concentration of a user. The apparatus also includes a breath interface, a wireless communication device, an alcohol sensor module and a microcontroller. The protective case houses and protects the portable computing device and the internal electronic components. The breath interface allows the user to provide a breath sample to the alcohol sensor module. The alcohol sensor module measures the alcohol concentration of the breath sample. The microcontroller operates the alcohol sensor module and conveys the alcohol concentration measurements to the portable computing device via the wireless communication device. The microcontroller and the wireless communication device are both mounted within the protective case. The alcohol concentration measurement is used as input for a variety of software application which promote safe drinking and driving habits.

16 Claims, 11 Drawing Sheets

SECTION A-A

SECTION B-B

SECTION C - C

PROTECTIVE CASE WITH INTEGRATED BREATHALYZER

The current application claims a priority to the U.S. Provisional Patent application Ser. No. 62/025,184 filed on Jul. 16, 2014.

FIELD OF THE INVENTION

The present invention relates generally to portable computing device accessories. More specifically, the present invention is a protective case with an integrated breathalyzer which takes a user's breath sample as input and determines the blood alcohol concentration. Additionally, the present invention also embodies a gaming aspect that utilizes the information obtained from the breathalyzer to customize a gaming experience for the user to promote safe drinking and driving habits.

BACKGROUND OF THE INVENTION

In the United States, on average, a single household owns about 2.28 vehicles. This large amount of cars leads to various problems in a society and community, one of which is driving under the influence of alcohol. Every day, about 28 people die as a result of drunken driving accidents. Accidents caused by driving under the influence of alcohol claim thousands of lives per year and cost the U.S. hundreds of billions of dollars in damages. In recent years, a flux of programs and laws have been implemented, aimed at increasing awareness and reducing the instances of such behaviors. Programs include television advertisements, educational lectures, and social gatherings meant to educate the general public about the consequences of drinking under the influence. While drunk driving is a major problem in the U.S., most states do allow for marginal blood alcohol content while driving and because of this most people still drive under the influence because they believe that they are under the limit and are sober enough to operate a vehicle; this mindset is what leads to accidents, injuries, and deaths. The problem becomes educating the public about safe habits and regulations instead of just abstinence.

The present invention utilizes a fun and novel apparatus which promotes safe drinking and driving habits. The present invention integrates an easy to use and accurate breathalyzer into a protective case, in particular for a mobile device or computer tablet. The present invention allows the user to become aware of their relative sobriety as well as play an educational and fun game that is directly customized to their inebriated state.

DETAIL DESCRIPTIONS OF THE INVENTION

All illustrations of the drawings are for the purpose of describing selected versions of the present invention and are not intended to limit the scope of the present invention.

The present invention is a protective case for a portable computing device that includes an integrated breathalyzer and gaming feature. In particular, the present invention determines the blood alcohol concentration (BAC), of a user by analyzing a breath sample from the user. An alcohol sensor is integrated into the protective case and measures the concentration of alcohol in a user's breath sample. This concentration is then wirelessly transmitted to a coupled portable computing device where it is utilized for a variety of software applications. One of the main software application takes the provided alcohol concentration measurement and in conjunction with the user's physical characteristics accurately determines and displays the BAC of the user, although the user characteristics are not a requirement. Alternative software application use the information to customize a game for the user on the portable computing device; these games promote safe drinking and driving habits. While the present invention is described and illustrated as a case for a smart phone, this in no way is meant to limit the scope of the invention. The protective case and the associated games may be modified and adapted to a wide variety of portable computing devices. Portable computing devices include, but are not limited to, tablets, laptops, and various smart phones; smart phones include mobile phones of different shapes, sizes, makes, and operating systems.

Figure 1:
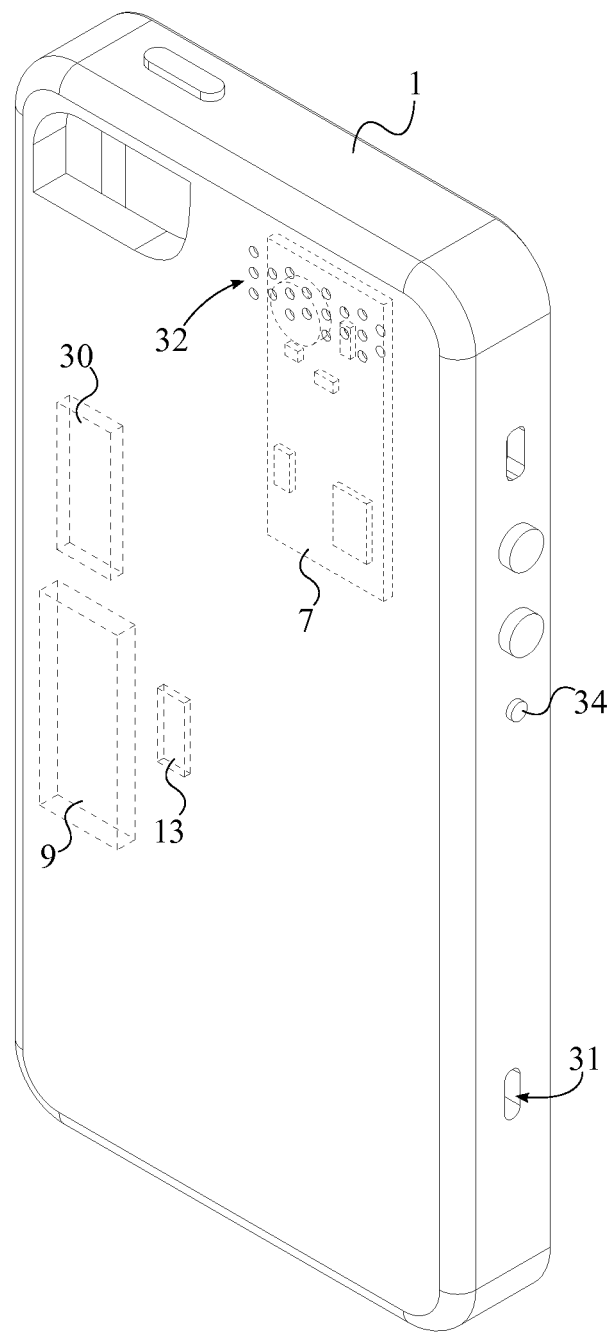
FIG. 1 is a perspective view of the preferred embodiment of the present invention.
Figure 2:
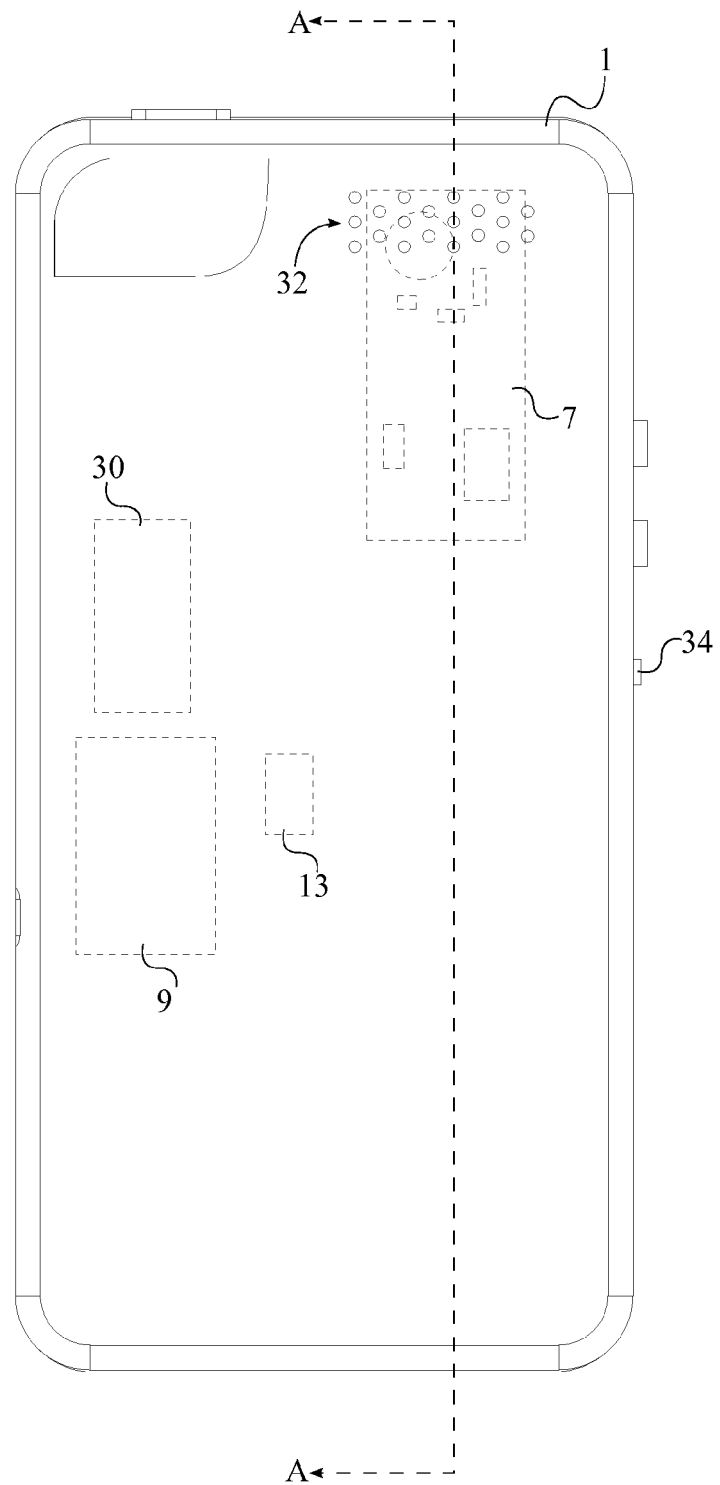
FIG. 2 is a front view of the preferred embodiment of the present invention.
Figure 3:
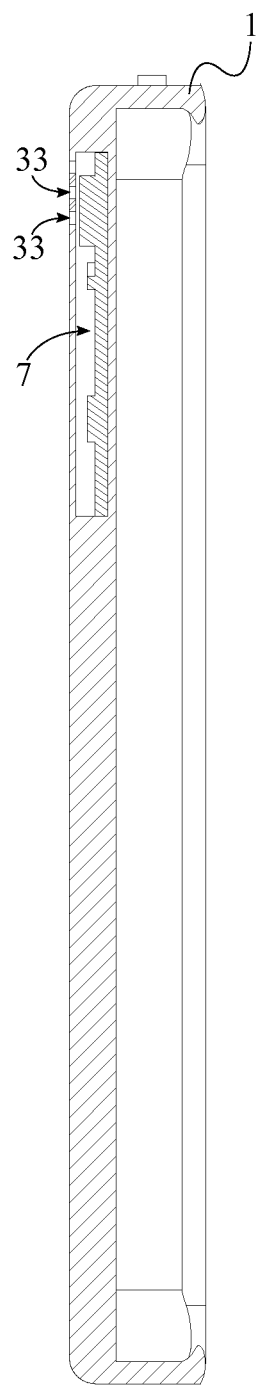
FIG. 3 is a sectional view taken along the line A-A shown in FIG. 2.

Referring to FIG. 1, the preferred embodiment of the present invention comprises a protective case 1, an alcohol sensor module 7, a breath interface 32, a wireless communication device 9, a microcontroller 13, a button switch 34, and a portable power source 30. The protective case 1 houses and physically protects the portable computing device, as well as contains the various components of the present invention. The alcohol sensor module 7 is an integrated circuit that measures the amount of alcohol particles present in a provided quantity of gas, more specifically the breath sample of the user. The alcohol sensor module 7 is mounted within the protective case 1. The breath interface 32 is the medium by which the user supplies his or her breath sample onto the alcohol sensor module 7 for analysis and processing. As such, the breath interface 32 is integrated into the protective case 1 and is in fluid communication with the alcohol sensor module 7. In the preferred embodiment, the breath interface 32 is a plurality of holes 33. The plurality of holes 33 traverses into the protective case 1, adjacent to the alcohol sensor module 7; more specifically, the plurality of holes 33 are located directly on top of the alcohol sensor module 7 as can be seen in FIG. 2. This exposes the alcohol sensor module 7 to the external environment and therefore allows a user to blow a breath sample directly onto the alcohol sensor module 7 as seen in FIG. 3.

The wireless communication device 9 allows for information to be wirelessly transferred in between the microcontroller 13 and the coupled portable computing device. The wireless communication device 9 is mounted within the protective case 1, out of sight of the user. Various different methods and components may be utilized for transmitting the data from the microcontroller 13 to the portable computing device.

Figure 11:
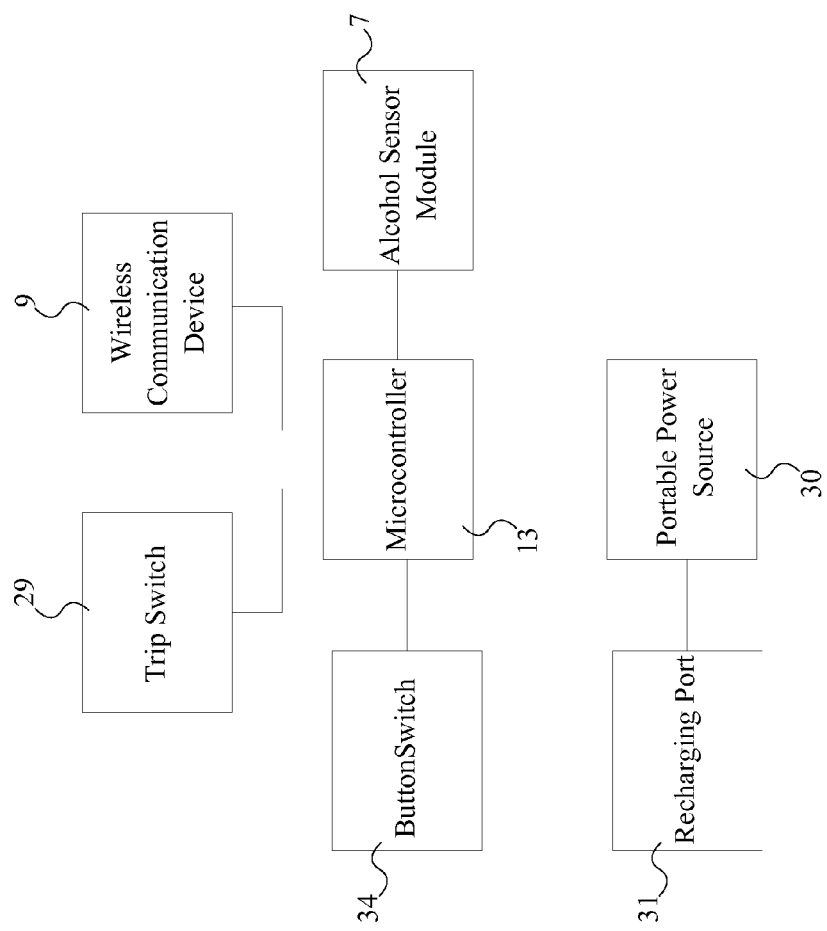
FIG. 11 is a schematic diagram of the present invention, depicting the electric and electronic connections in between the electrical components.

The portable power source 30 is mounted within the protective case 1 and is electrically connected to the microcontroller 13. The portable power source 30 provides the necessary electrical energy for the present invention. Preferably, the portable power source 30 is a rechargeable battery that is electrically connected to a recharging port 31. The recharging port 31 is mounted within the protective case 1 and allows the user to easily and quickly recharge the portable power source 30. The microcontroller 13 distributes and controls the flow of electricity to the various electrical components, seen in FIG. 11, in order to execute the functions of the present invention. More specifically, the microcontroller 13 is electronically connected to the wireless communication device 9 and the alcohol sensor module 7. The microcontroller 13 and the wireless communication device 9 are mounted within the protective case 1 as not to alter the handling characteristics of the protective case 1. The button switch 34 turns the present invention on and off. The button switch 34 is integrated into the protective case 1 and is also electronically connected to the microcontroller 13; preferably positioned on the side of the protective case 1 in order to prevent accidental actuation.

The alcohol sensor module 7 uses a semiconductor sensing element in order to measure the alcohol concentration in a sample of gas, in particular the user's breath sample. More specifically, the alcohol sensor module includes a metal oxide gas sensor. This type of module is ideal because it is highly sensitive, fast, responsive, has a relatively long life span, is small in size, and has a relatively low cost. The alcohol sensor module 7 also includes the necessary supporting circuitry required for the operation of the semiconductor sensing element. The supporting circuitry records the change in resistance, and performs other similar functions. The electrical resistance of the semiconductor sensing element proportionately changes according to the alcohol concentration in the sample of gas. More specifically, the change in resistance of the semiconductor sensing element is inversely proportional to the alcohol concentration of the sample of gas. This characteristic allows for accurate measurement of alcohol concentration in a gas. The alcohol sensor module 7 measures the change in electric resistance of the semiconductor sensing element once it is exposed to the sample of gas, the breath sample, and outputs a corresponding voltage. The microcontroller 13 utilizes the voltage to calculate the BAC value. The BAC value is then wirelessly transmitted to the coupled portable computing device via wireless communication device 9. The BAC value is then used as input for the software application of the present invention for various functions for the user. The preferred alcohol sensor module 7 is a Metal Oxide (MOX) based gas sensor module. Additionally, the present invention also utilizes a hotplate fabricated using robust silicon dioxide membrane which includes a tungsten based heating element for the MOX gas sensor. In particular, the preferred alcohol sensor module 7 is the CCS803 gas sensor due to its ultra-low power consumption, fast response time, and miniature size. The CCS803 gas sensor is capable to detect Ethanol in the range of 10 to 600 parts per million. Alternative methods and devices may be used for the alcohol sensor module 7. For example, in one embodiment of the present invention a tin oxide ($SnO_2$) based sensor module is used.

To operate the preferred embodiment of the present invention, the user simply actuates the button switch 34 on the protective case 1, aligns his or her lips adjacent to the plurality of holes 33, and blows for a predetermined amount of time. This provides the alcohol sensor module with a breath sample to analyze.

Figure 4:
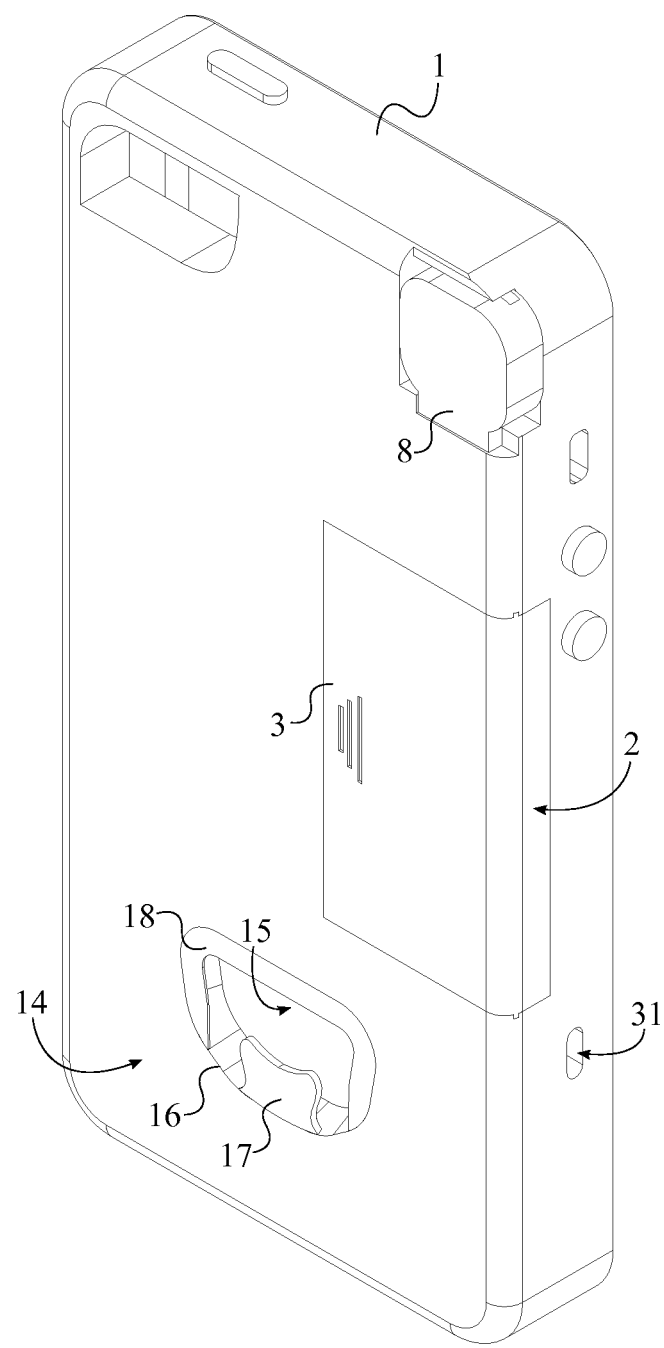
FIG. 4 is a perspective view of an alternative embodiment of the present invention in the closed configuration.
Figure 6:
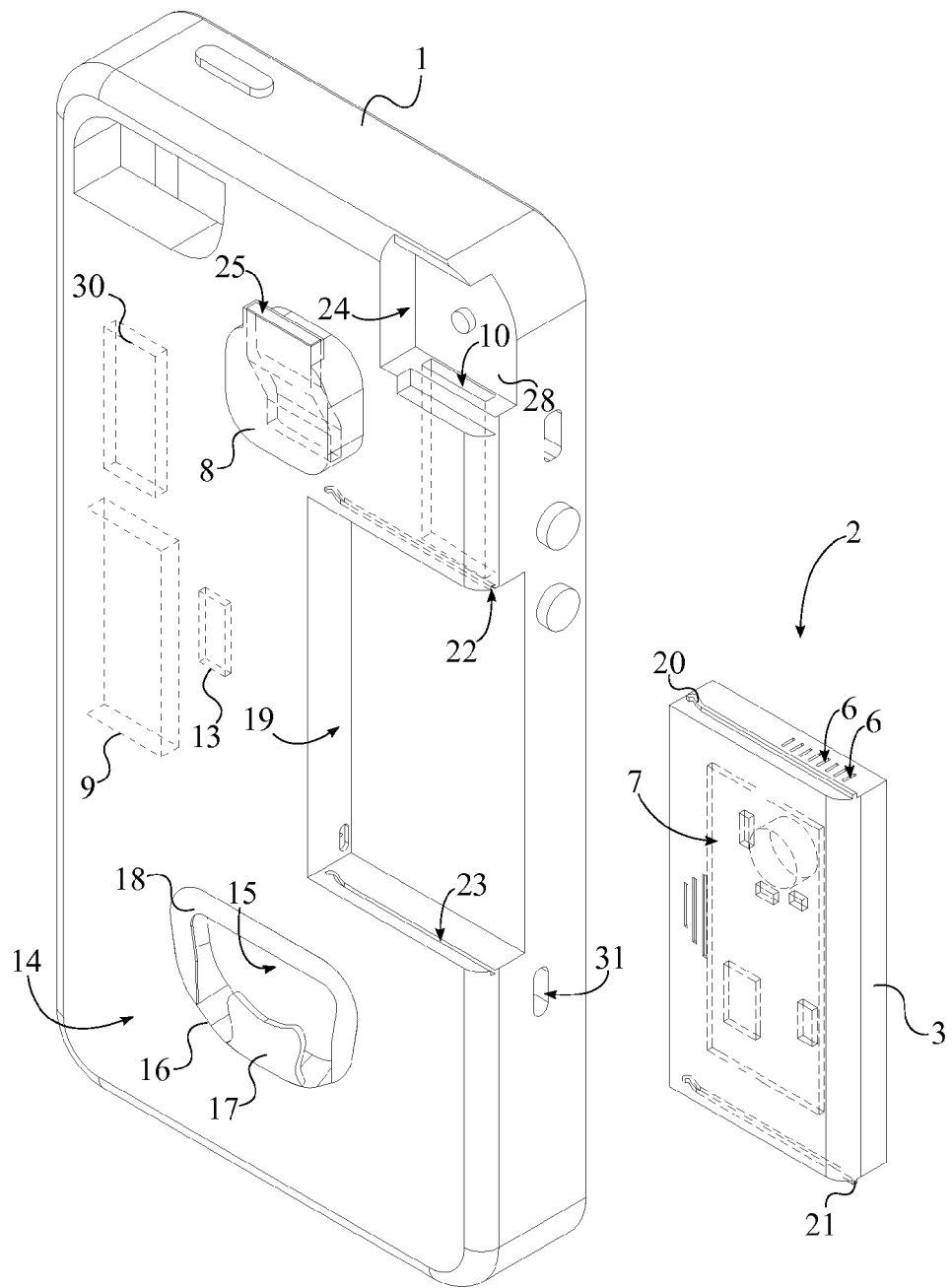
FIG. 6 is an exploded perspective view of the alternative embodiment of the present invention.
Figure 7:
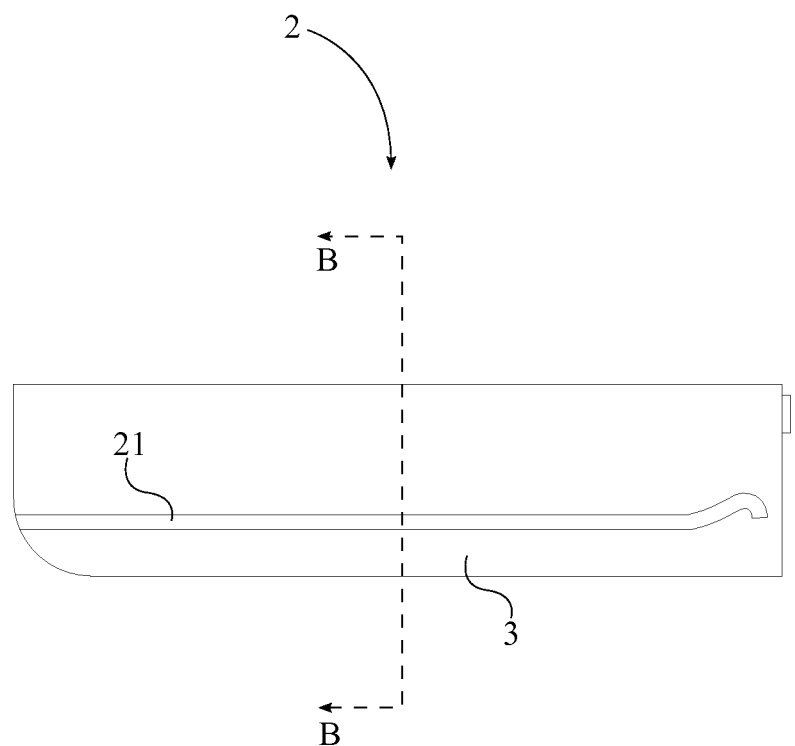
FIG. 7 is a side-view of the breathalyzer assembly.
Figure 8:
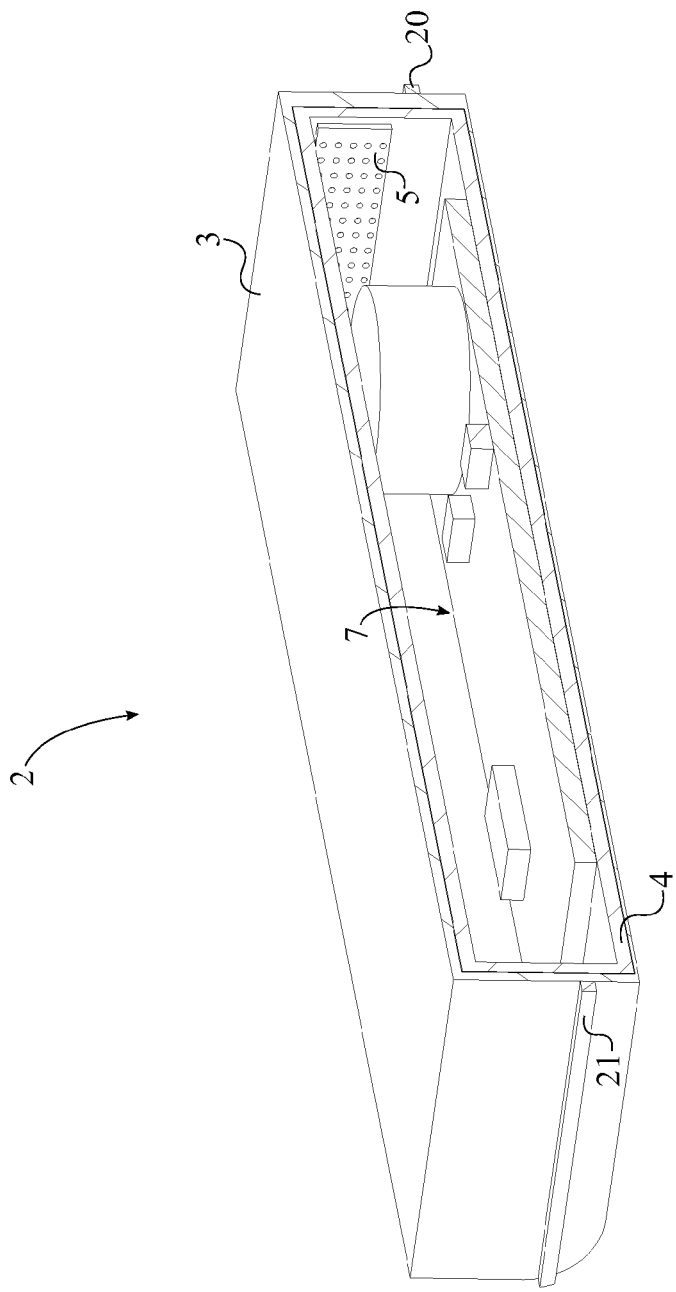
FIG. 8 is a perspective sectional view taken along the line B-B shown in FIG. 7.

In an alternative embodiment of the present invention, a breathalyzer assembly 2 is used to house and protect the alcohol sensor module 7 as seen in FIG. 4 and FIG. 6. The breathalyzer assembly 2 comprises a separable housing 3, an insulating layer 4, a plurality of air vents 6, and a filter screen 5. As such, the alcohol sensor module 7 is mounted within the separable housing 3; the separable housing 3 physically protects the alcohol sensor module 7. The separable housing 3 is in turn attached into the protective case 1, preferably in a flush manner so as not to interfere with the handling characteristics of the proactive case 1. In this embodiment, the breath interface 32 comprises a mouthpiece 8 and a duct 10 to allow the user to provide the breath sample to the alcohol sensor module 7. The mouthpiece 8 is adjacently connected into the protective case 1 and is the physical interface which the user may place his or her lips upon when providing the breath sample for the present invention. The duct 10 traverses through the protective case 1 with an input 11 of the duct 10 being adjacently positioned to the mouthpiece 8 and an output 12 of the duct 10 being adjacently positioned to the separable housing 3. The duct 10 puts the mouthpiece 8 and the separable housing 3 in fluid communication with each other. The insulating layer 4 is internally superimposed over the separable housing 3 as seen in FIG. 7 and FIG. 8. The insulating layer 4 protects the protective case 1 and the user from possible high temperatures produced by the alcohol sensor module 7. The type of material used for the insulating layer 4 may vary depending on the type of the alcohol sensor module 7 used. The plurality of air vents 6 traverses laterally into the separable housing 3 and through the insulating layer 4. The plurality of air vents 6 is adjacently positioned to the output 12 of the duct 10 such that the user's breath sample may flow into the separable housing 3 to reach the alcohol sensor module 7. The filter screen 5 prevents contaminates such as smoke, dust, and debris from reaching the alcohol sensor module 7; and is adjacently connected across the plurality of air vents 6.

The separable housing 3 acts as a cartridge for the present invention and allows the user to replace the alcohol sensor module 7 without requiring the user to buy a new protective case 1. This is useful if the alcohol sensor 7 module malfunctions or breaks. In some embodiments, the present invention may utilize an alternative alcohol sensor module 7 that has a limited amount of uses and requires the user to replace the cartridge, more specifically the breathalyzer assembly. The separable housing 3 is attached to the protective case 1 through the use of a receptive cavity 19 and a track system. The receptive cavity 19 traverses into the protective case 1, preferably into the backing of the protective case 1 for quick and easy access. The receptive cavity 19 is sized and shaped to the separable housing 3 such that the separable housing 3 sits flush with the exterior surfaces of the protective case 1 as seen in FIG. 4 and FIG. 6. The separable housing 3 is attached into the receptive cavity 19 through the use of a first rail 20, a second rail 21, a first recession 22, and a second recession 23. Both the first recession 22 and the second recession 23 traverse into the protective case 1 from the receptive cavity 19 and are positioned opposite to each other across the receptive cavity 19. The first rail 20 and the second rail 21 are positioned on the separable housing 3 complimentary to the location of the first recession 22 and the second recession 23, respectively. The first rail 20 is adjacently connected to the separable housing 3. The second rail 21 is adjacently connected to the separable housing 3, opposite the first rail 20. The separable housing 3 is attached to the protective case 1 by the first rail 20 being engaged to the first recession 22 and the second rail 21 being engaged to the second recession 23. This design allows the separable housing 3 to slide in and attach to the protective case 1 quickly and easily without requiring any tools. The user simply aligns the first rail 20 and the second rail 21 to the respective first recession 22 and second recession 23 and slides the separable housing 3 towards the center of the protective case 1 until the separable housing 3 sits flush with the adjacent side and back surface of the protective case 1 as seen in FIG. 4. Alternative attachment/fastening means may also be utilized including, but not limited to, magnets, latches, buttons, and adhesive.

Figure 9:
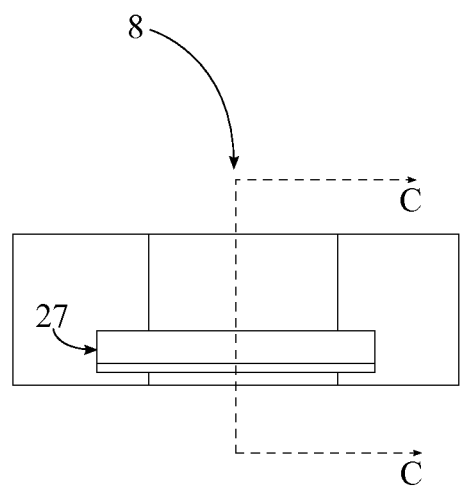
FIG. 9 is a front view of the mouthpiece component of the present invention.
Figure 10:
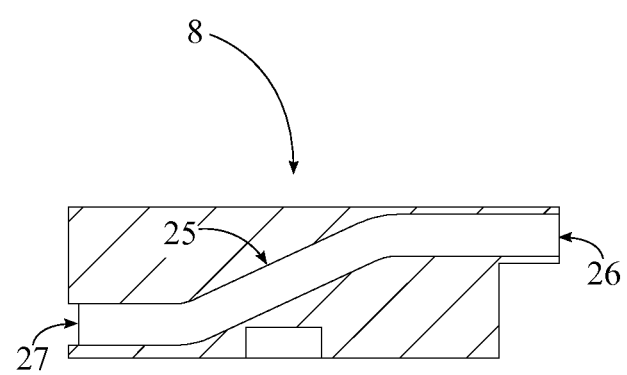
FIG. 10 is sectional view taken along the line C-C shown in FIG. 9.

The mouthpiece 8 is integrated into the protective case 1 through a mouthpiece-receptive cavity 24. The mouthpiece-receptive cavity 24 traverses into the protective case 1 and is shaped to receive the mouthpiece 8. The mouthpiece-receptive cavity 24 is preferably positioned at the top right or left corner of the backing of the protective case 1 as this design provides the user easier access to the mouthpiece 8. The mouthpiece 8 is pivotally connected to a bottom surface 28 of the mouthpiece-receptive cavity 24 and comprises a breath channel 25. The breath channel 25 laterally traverses through the mouthpiece 8 as seen in FIG. 9 and FIG. 10; and facilitates the flow of air from the user's mouth to the duct 10 and resultantly to the alcohol sensor module 7. An input 26 of the breath channel 25 is positioned offset from the bottom surface 28. An output 27 of the breath channel 25 is positioned adjacent to the bottom surface 28, therefore offsetting the input 26 and the output 27 of the breath channel 25 a certain distance apart. The offset design allows the mouthpiece 8 and the protective case 1 to be positioned into two configurations, an operative configuration and a closed configuration.

Figure 5:
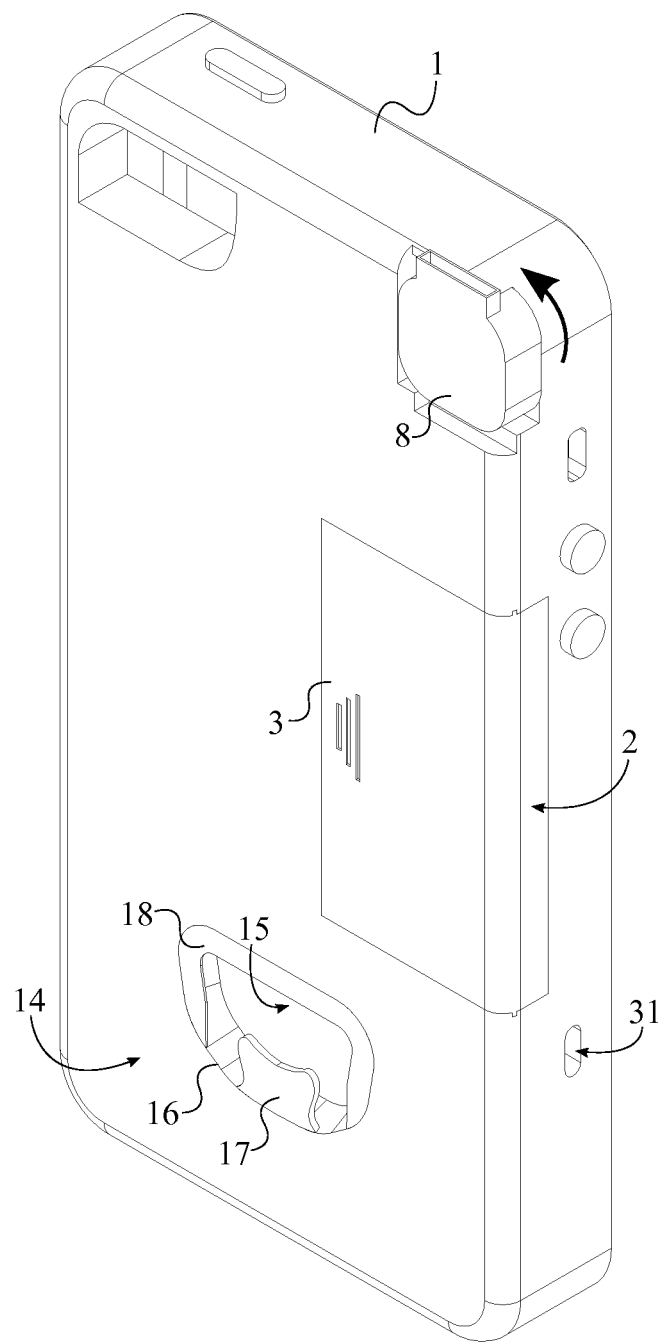
FIG. 5 is a perspective view of the alternative embodiment of the present invention in the operative configuration.
Figure 12:
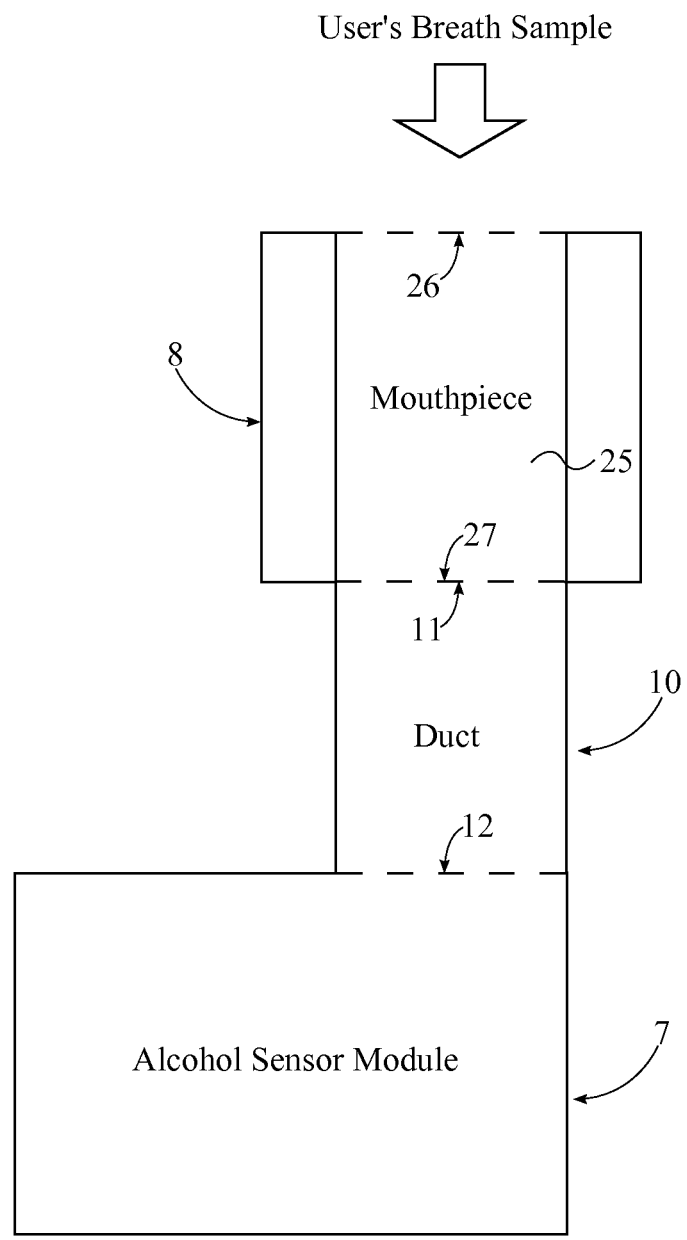
FIG. 12 is a schematic diagram of the alternative embodiment of the present invention, depicting the fluid connections between the mouthpiece, duct, and alcohol sensor module.

In the operative configuration, the output 27 of the breath channel 25 is positioned to be in fluid communication with the input 11 of the duct 10; and the input 26 of the breath channel 25 is oriented away from the protective case 1, open to the environment and the user as seen in FIG. 5. The fluid communication is depicted in FIG. 12, a fluid schematic of the present invention. Additionally, when the mouthpiece 8 and the protective case 1 are positioned into the operative configuration, the associated electronic components of the present invention are activated through a trip switch 29, rather than a button switch 34 as seen in the preferred embodiment of the present invention. The trip switch 29 is integrated into the protective case 1, adjacent to the mouthpiece-receptive cavity 24, and is electronically connected to the microcontroller 13. The trip switch 29 is also operatively engaged to the mouthpiece 8. The trip switch 29 activates the microcontroller 13 and the associated electronic components when the mouthpiece 8 is rotated into the operative configuration. Additionally, the trip switch 29 is used to begin measurement. Furthermore, the trip switch 29 may also be used for wireless communication pairing between the wireless communication device 9 and the portable computing device. In the closed configuration, the input 26 of the breath channel 25 is oriented towards the input 11 of the duct 10 as seen in FIG. 4, closing off access to the duct 10.

To operate the alternative embodiment of the present invention, the user first rotates the mouthpiece 8 180 degrees such that the input 26 of the breath channel 25 is facing away from the protective case 1. This movement triggers the trip switch 29, which turns on the internal electronic components of the present invention and begins to heat up the semiconductor sensing element to the appropriate temperature. Next, the user simply blows into the mouthpiece 8 for a certain amount of time. While the user blows into the mouthpiece 8, the alcohol sensor module 7 measures the alcohol concentration in the provided gas. This measurement is then sent to the portable computing device by the wireless communication device 9 where the BAC of the user is calculated and displayed.

As mentioned above, the present invention also includes a software component which takes the raw data from the breathalyzer assembly 2 and descriptive information from the user to accurately determine the BAC of the user. The software components may be implemented in the form of a software application on the portable computing device. The portable computing device receives alcohol concentration measurements from the breathalyzer assembly 2 and feeds said information into the software application. Additionally, the software application may also use descriptive information of the user to more accurately predict the BAC of the user. Descriptive information may include, but is not limited to, age, height, weight, race, gender, number of drinks consumed, and type of drinks consumed. In one embodiment, the software application takes the aforementioned information, calculates the BAC, and displays the results to the screen of the portable computing device. In another embodiment, the aforementioned information is not required for the present invention to calculate and display the BAC. The software application may also include additional features which either entertain and or educate the user about drinking and driving habits.

In one embodiment, the present invention also includes a bottle opener 14 integrated into the protective case 1. The bottle opener 14 allows the user to remove metal bottle caps from bottles, increasing the versatility of the present invention. The bottle opener 14 is preferably integrated into a backing of the protective case 1 for easier access and increased leverage. The bottle opener 14 comprises a cap-receptive cavity 15, a cap-engagement lip 17, and a fulcrum region 18. The cap-receptive cavity 15 traverses into the protective case 1 and is sized to receive at least half of a standard bottle cap. The fulcrum region 18 is adjacently connected to a rim 16 of the cap-receptive cavity 15 as seen in FIG. 4. The fulcrum region 18 is a flange protruding from the rim 16 towards the center of the cap-receptive cavity 15 that engages the top of the bottle cap and provides a pivot point about which the bottle is rotated to remove the bottle cap. The cap-engagement lip 17 is adjacently connected to the rim 16 and positioned opposite to the fulcrum region 18 across the cap-receptive cavity 15. The cap-engagement lip 17 is designed to engage the lower edge of the rim of the bottle cap. To prevent deformation and structural failure, it is preferred that the fulcrum region 18 and the cap-engagement lip 17 be composed of a strong durable material. Materials include, but are not limited to, steel, titanium, and iron.

The present invention also includes a gaming feature. The gaming feature uses the calculated BAC of the user to customize an interactive and educational game for the user to play. In one embodiment of the present invention, the gaming features includes the user controlling a car on the portable computing device through tilt technology in various environments. The game environment, driving aspects, blurriness, and all around atmosphere are designed to directly reflect the perspective of a driver with an equal inebriation level as the user's BAC. For example, the higher the user's BAC, the slower the car's reaction will be to the user's input. Additionally, the car may begin to arbitrarily swerve in various directions to simulate an inebriated driver. In one option, the user must control the car and ensure that it does not veer out of the lane while simultaneously avoiding obstacles such as ducks, bikes, pedestrians, and other cars. Additionally, police cars may intervene and or set up driving under the influence (DUI) check-stations throughout each course that, if run into, will end the game for the user. One particular version requires the user to avoid obstacles and if three obstacles are hit then the user loses the game. The ending score, dependent on distance traveled and obstacles passed, is multiplied by $[1/((0.2-BAC)^2)]$ where BAC is the calculated readout at the beginning. Alternative means for calculating the score may also be used. Any information from the game and the present invention may be shared on social networks; furthermore, in one embodiment, the user may play online with other players. The main purpose of the gaming feature is to promote safe drinking and driving habits. The game will most often end with the statement "Games don't have consequences. Life's not a game. Don't drink and drive.".

The gaming feature also includes a timer which prevents the user from resetting the game before the sensor is ready for another measurement; some types of alcohol sensors require time for re-ionization. Additionally, the present invention may also calculate and display the average time the user would need to sober up. Simple charts based on sex, weight, height, etc. may also be available and utilized in the present invention to further educate the user on the effects of alcohol and driving under the influence. Other games associated with the breathalyzer case may also be sold to the user, each with their own purpose, designs, and implementation.

In one embodiment of the present invention, the software application aids the user in calling him/her a taxi cab. To accomplish this, the software application may utilize the global positioning system (GPS) location of the portable computing device to hail a taxi cab to the location of the portable computing device. The present invention may also be compatible with a variety of transportation network companies to further facilitate transportation for the user.

Although the invention has been explained in relation to its preferred embodiment, it is to be understood that many other possible modifications and variations can be made without departing from the spirit and scope of the invention as hereinafter claimed.

What is claimed is:

1. A protective case with integrated breathalyzer for a portable computing device comprises:
   a protective case;
   a wireless communication device;
   a breath interface;
   a microcontroller;
   an alcohol sensor module;
   the microcontroller, the alcohol sensor module, and the wireless communication device being mounted within the protective case;
   the microcontroller being electronically connected to the wireless communication device and the alcohol sensor module;
   the breath interface being integrated into the protective case;
   the breath interface being in fluid communication with the alcohol sensor module;
   a breathalyzer assembly;
   the breathalyzer assembly comprises a housing;
   the alcohol sensor module being mounted within the housing;
   the housing being attached into the protective case;
   a first rail;
   a second rail;
   a first recession;
   a second recession;
   the first recession traversing into the protective case from the receptive cavity;
   the second recession traversing into the protective case from the receptive cavity;
   the first recession and the second recession being positioned opposite to each other about the receptive cavity;
   the first rail being adjacently connected to the housing;
   the second rail being adjacently connected to the housing, opposite the first rail;
   the first rail being engaged to the first recession;
   the second rail being engaged to the second recession; and
   wherein the alcohol sensor module being a Metal Oxide (MOX) based gas sensor module.

2. The protective case with integrated breathalyzer for a portable computing device as claimed in claim 1 comprises:
   the breath interface comprises a plurality of holes; and
   the plurality of holes traversing into the protective case, adjacent to the alcohol sensor module.

3. The protective case with integrated breathalyzer for a portable computing device as claimed in claim 1 comprises:
   a bottle opener;
   the bottle opener comprises a cap-receptive cavity, a cap-engagement lip, fulcrum region;
   the cap-receptive cavity traversing into the protective case;
   the fulcrum region being adjacently connected to a rim of the cap-receptive cavity;
   the cap-engagement lip being adjacently connected to the rim; and
   the fulcrum region and the cap-engagement lip being positioned opposite to each other across the cap-receptive cavity.

4. The protective case with integrated breathalyzer for a portable computing device as claimed in claim 1 comprises:
   the breath interface comprises a mouthpiece and a duct;
   the mouthpiece being adjacently connected into the protective case;
   the duct traversing through the protective case;
   an input of the duct being adjacently positioned to the mouthpiece;
   an output of the duct being adjacently positioned to the housing; and
   the housing being separable.

5. The protective case with integrated breathalyzer for a portable computing device as claimed in claim 4 comprises:
   a receptive cavity;
   the receptive cavity traversing into the protective case; and
   the housing being attached into the receptive cavity.

6. The protective case with integrated breathalyzer for a portable computing device as claimed in claim 4 comprises:
   the breathalyzer assembly further comprises an insulating layer, a filter screen, and a plurality of air vents;
   the insulating layer being internally superimposed over the housing;
   the plurality of air vents laterally traversing into the housing and through the insulating layer;
   the plurality of air vents being adjacently positioned to the output of the duct; and
   the filter screen being adjacently connected across the plurality of vents.

7. The protective case with integrated breathalyzer for a portable computing device as claimed in claim 4 comprises:
   a mouthpiece-receptive cavity;
   the mouthpiece comprises a breath channel;
   the mouthpiece-receptive cavity traversing into the protective case;

the mouthpiece being pivotally connected to a bottom surface of the mouthpiece-receiving cavity;

the breath channel laterally traversing through the mouthpiece;

an input of the breath channel being positioned offset from the bottom surface; and an output of the breath channel being positioned adjacent to the bottom surface.

8. The protective case with integrated breathalyzer for a portable computing device as claimed in claim 7 comprises:

a trip switch;

wherein the mouthpiece and the protective case are in an operative configuration;

the output of the breath channel being in fluid communication with the input of the duct;

the trip switch being integrated into the protective case, adjacent to the mouthpiece-receiving cavity;

the trip switch being electronically connected to the microcontroller; and the trip switch being operatively engaged to the mouthpiece.

9. The protective case with integrated breathalyzer for a portable computing device as claimed in claim 1 comprises:

a button switch;

the button switch being integrated into the protective case; and the button switch being electronically connected to the microcontroller.

10. The protective case with integrated breathalyzer for a portable computing device as claimed in claim 1 comprises:

a portable power source;

the portable power source being mounted within the protective case; and the portable power source being electrically connected to the microcontroller.

11. The protective case with integrated breathalyzer for a portable computing device as claimed in claim 10 comprises:

a recharging port;

the recharging port being mounted within the protective case; and the recharging port being electrically connected to the portable power source.

12. A protective case with integrated breathalyzer for a portable computing device comprises:

a protective case;
a wireless communication device;
a breath interface;
a microcontroller;
an alcohol sensor module;

the microcontroller, the alcohol sensor module, and the wireless communication device being mounted within the protective case;

the microcontroller being electronically connected to the wireless communication device and the alcohol sensor module;

the breath interface being integrated into the protective case;

the breath interface being in fluid communication with the alcohol sensor module;

the breath interface comprising a plurality of holes;

the breath interface comprises a plurality of holes;

the plurality of holes traversing into the protective case, adjacent to the alcohol sensor module;

a bottle opener;

the bottle opener comprises a cap-receptive cavity, a cap-engagement lip, fulcrum region;

the cap-receptive cavity traversing into the protective case;

the fulcrum region being adjacently connected to a rim of the cap-receptive cavity;

the cap-engagement lip being adjacently connected to the rim; and the fulcrum region and the cap-engagement lip being positioned opposite to each other across the cap-receptive cavity.

13. The protective case with integrated breathalyzer for a portable computing device as claimed in claim 12 comprises:

a button switch;

the button switch being integrated into the protective case; and the button switch being electronically connected to the microcontroller.

14. The protective case with integrated breathalyzer for a portable computing device as claimed in claim 12 comprises:

a portable power source;

the portable power source being mounted within the protective case; and the portable power source being electrically connected to the microcontroller.

15. The protective case with integrated breathalyzer for a portable computing device as claimed in claim 14 comprises:

a recharging port;

the recharging port being mounted within the protective case; and the recharging port being electrically connected to the portable power source.

16. The protective case with integrated breathalyzer for a portable computing device as claimed in claim 12, Wherein the alcohol sensor module is a MOX based gas sensor module.

\* \* \* \* \*